US008173616B2

(12) United States Patent
Anderson et al.

(10) Patent No.: US 8,173,616 B2
(45) Date of Patent: May 8, 2012

(54) RNA-INDUCED TRANSLATIONAL SILENCING AND CELLULAR APOPTOSIS

(75) Inventors: Paul Anderson, Belmont, MA (US); Satoshi Yamasaki, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 12/990,493

(22) PCT Filed: May 1, 2009

(86) PCT No.: PCT/US2009/002718
§ 371 (c)(1),
(2), (4) Date: Oct. 29, 2010

(87) PCT Pub. No.: WO2009/134443
PCT Pub. Date: Nov. 5, 2009

(65) Prior Publication Data
US 2011/0046209 A1     Feb. 24, 2011

Related U.S. Application Data

(60) Provisional application No. 61/071,522, filed on May 2, 2008.

(51) Int. Cl.
*A61K 31/70* (2006.01)
*C07H 21/02* (2006.01)
*C07H 21/04* (2006.01)
(52) U.S. Cl. ..................... 514/44 A; 536/24.1; 536/24.5
(58) Field of Classification Search .................... 514/44; 536/24.5
See application file for complete search history.

(56) References Cited

U.S. PATENT DOCUMENTS

| 7,056,704 | B2 | 6/2006 | Tuschl et al. |
| 7,078,196 | B2 | 7/2006 | Tuschl et al. |
| 7,232,806 | B2 | 6/2007 | Tuschl et al. |

FOREIGN PATENT DOCUMENTS

| EP | 1 681 347 A1 | 7/2006 |
| WO | WO 93/23569 | 11/1993 |
| WO | WO 94/02595 | 2/1994 |
| WO | WO 99/04819 | 2/1999 |
| WO | WO 99/05094 | 2/1999 |

OTHER PUBLICATIONS

Yamasaki et al. J. Cell Biol. vol. 185, No. 1, pp. 35-42 (2009).*
Fu et al. FEBS Letters, vol. 583, pp. 437-442, (2009).*
International Search Report for PCT/US2009/002718 filed May 1, 2009.
Written Opinion of the International Searching Authority for PCT/US2009/002718 filed May 1, 2009.
International Preliminary Report on Patentability for PCT/US2009/002718 filed May 1, 2009.

Ambros, "The functions of animal microRNAs," *Nature* 431:350-355 (Sep. 2004).
Akhtar, et al., "Cellular uptake and antisense oligonucleotides," *Trends Cell Biol.* 2:139-144 (May 1992).
Bentwich, et al., "Identification of hundreds of conserved and nonconserved human microRNAs," *Nature Genetics* 37(7):766-770 (Jul. 2005).
Brennecke, et al., "Discrete Small RNA-Generating Loci as Master Regulators of Transposon Activity in *Drosophlia*," *Cell* 128:1089-1103 (Mar. 2007).
Fire, et al., "Potent and specific genetic interference by double-stranded RNA in *Caenorhabditis elegans*," *Nature* 391:806-811 (1998).
Garcia, et al., "The dsRNA protein kinase PKR: Virus and cell control," *Biochimie* 89:799-811 (2007).
Girard, et al., "A germline-specific class of small RNAs binds mammalian Piwi proteins," *Nature* 442:199-202 (Jul. 2006).
Grivna, et al., "MIWI associates with translational machinery and PIWI-interacting RNAs (piRNAs) in regulating spermatogenesis," *PNAS* 103(36):13415-13420 (Sep. 2006).
Hannon, et al., "Unlocking the potential of the human genome with RNA interference," *Nature* 431:371-378 (Sep. 2004).
Hershey, et al., "Translation Control in Mammalian Cells," *Annu. Rev. Biochem.* 60:717-755 (1991).
Iordanov, et al., "Molecular Determinants of Apoptosis Induced by the Cytotoxic Ribonuclease Onconase: Evidence for Cytotoxic Mechanisms Different from Inhibition," *Cancer Res.* 60:1983-1994 (Apr. 2000).
Iordanov, et al., "Ultraviolet Radiation Triggers the Ribotoxic Stress Response in Mammalian Cells," *J Biol. Chem.* 273(25):15794-15803 (Jun. 1998).
Kawaji, et al., "Hidden layers of human small RNAs," *BMC Genomics* 9:157 (Apr. 2008).
Lau, et al., "Characterization of the piRNA Complex from Rat Testes," *Science* 313:363-367 (Jul. 2006).
Lee, et al., "Starvation-induced Cleavage of the tRNA Anticodon Loop in *Tetrahymena thermophilia*," *J. Biol. Chem.* 280(52):42744-42749 (Dec. 2005).
Mattick, "Non-coding RNAs: the architects of eukaryotic complexity," *EMBO Reports* 2(11):986-991 (2001).
McEwen, et al., "Heme-regulated Inhibitor Kinase-mediated Phosphorylation of Eukaryotic Translation Initiation Factor 2 Inhibits Translation, Induces Stress Granule Formation, and Mediates Survival upon Arsenite Exposure," *J. Biol. Chem.* 280(17):16925-16933 (2005).
Milligan, et al., "Oligoribonucleotide synthesis using T7 RNA polymerase and synthetic DNA templates," *Nucleic Acids Research* 15(21):8783-8798 (1987).
Rocha, et al.,"Effects of trichothecene mycotoxins on eukaryotic cells: A review," *Food Additives and Contaminants* 22(4):369-378 (2005).

(Continued)

*Primary Examiner* — Terra Cotta Gibbs
(74) *Attorney, Agent, or Firm* — Law Office of Michael A. Sanzo, LLC

(57) ABSTRACT

The invention is directed to RNA molecules that can be used to inhibit protein synthesis and to induce cells to undergo apoptosis. It also includes pharmaceutical compositions containing the RNAs that can be used in treating or preventing tumors; abnormal dermatological growths and viral infections.

20 Claims, No Drawings

OTHER PUBLICATIONS

Ron, et al., "Signal integration in the endoplasmic reticulum unfolded protein response," *Nature Reviews: Mol. Cell Biol.* 8:519-529 (2007).

Scaringe, et al., "Chemical synthesis of biologically active oligoribonucleotides using β-cyanoethyl protected ribonucleoside phosphoramidites," *Nucleic Acids Research* 18(18):5433-5441 (1990).

Shifrin, et al., "Trichothecene Mycotoxins Trigger a Ribotoxic Stress Response That Activates c-Jun N-terminal Kinases and p38 Mitogen-activated Protein Kinase and Induces Apoptosis," *J. Biol. Chem.* 274(20):13985-13992 (1999).

Tenson, et al., "Antibiotics and the ribosome," *Mol. Microbiol.* 59(6):1664-1677 (2006).

Usman, et al., "Automated Chemical Synthesis of Long Oligoribonucleotides Using 2'-O-Silylated Ribonucleoside 3'-O-Phosphoramidites on a Controlled-Pore Glass Support: Synthesis of a 43-Nucleotide Sequence Similar to the 3'-Half Molecule of an *Escherichia coli* Formylmethionine tRNA[1]," *J. Am. Chem. Soc.* 109:7845-7854 (1987).

Wincott, et al., "Synthesis, deprotection, analysis and purification of RNA and ribozymes," *Nucleic Acids Research* 23(14):2677-2684 (1995).

Wincott, et al., "A Practical Method for the Production of RNA and Ribozymes," *Methods Mol. Biol.* 74:59-68 (1997).

Zamor, et al., "RNAi: Double-Stranded RNA Directs the ATP-Dependent Cleavage of mRNA at 21 to 23 Nucleotide Intervals," *Cell* 101:25-33 (2000).

\* cited by examiner

RNA-INDUCED TRANSLATIONAL SILENCING AND CELLULAR APOPTOSIS

CROSS REFERENCE TO RELATED APPLICATIONS

The present application is US national stage of international application PCT/US2009/002718, which had an international filing date of May 1, 2009 and claims the benefit of U.S. provisional application 61/071,522, filed on May 2, 2008, which is incorporated herein by reference in its entirety. The PCT application was published in English under PCT Article 21(2) on Nov. 5, 2009.

STATEMENT OF GOVERNMENT FUNDING

This invention was made with Government support under Grant Nos. AI065858, AR051472, and AI033600 awarded by the National Institutes of Health. The Government has certain rights in this invention.

FIELD OF THE INVENTION

The present invention is directed to short RNA molecules that can be used to inhibit protein synthesis and induce cellular apoptosis. These RNAs may be used in studying post-transcriptional processes involved in controlling gene expression and in therapies designed to kill tumor cells or inhibit virus growth.

BACKGROUND OF THE INVENTION

Among the most significant discoveries of the last decade was that of RNA-based mechanisms of post-transcriptionally regulating gene expression (Hamilton, et al., *Nature* 431:371-378 (2004); Fire, et al., 391:806-811 (1998); Zamor, et al., *Cell* 101:25-33 (2000). It has been found that, when double stranded RNA enters cells, e.g., due to viral infection, it is recognized and cleaved by specific "dicer enzymes" into fragments (siRNAs) 21-25 nucleotides in length with 3' dinucleotide overhangs. These fragments bind to a protein complex (RISC) that causes the RNA to unwind and one of the strands, the passenger strand, to be degraded. The remaining sequence targets the complex to an mRNA having a complementary sequence which is then cleaved. As a result, the expression of protein encoded by that mRNA is prevented.

Primitive cells and organisms may have used this system to protect themselves from virus infection long before the development of adaptive immune systems. Higher organisms appear to have adapted the system to modulating gene expression. In humans for example, endogenous genomic sequences transcribe RNA capable of folding back on itself to form double stranded regions. These are cleaved by enzymes to form "miRNA" fragments that then act in essentially the same manner as siRNAs. However, unlike siRNAs, the miRNAs often contain mismatches that do not allow the cleavage of mRNA targets. Rather, partially complementary target mRNAs are deadenylated, decapped, and degraded by the 5'-3' exonucleolytic pathway. Alternatively, these mRNAs can be subject to translational silencing by a mechanism that is poorly characterized (for overview see, Ambros, *Nature* 431:350-355 (2004); Mattick, *EMBO Reports* 2:986-991 (2001); Bentwick, et al., *Nature Genetics* 37:766-770 (2005)).

The process of catalytically shutting down the translation of specific mRNAs by introducing double stranded RNA into cells can be used to target essentially any chosen target transcript. Thus, RNA interference is a technique of great interest clinically (where genes associated with diseases may be targeted) and to researchers attempting to identify the function of genes, e.g., resulting from the human genome project (see generally U.S. Pat. Nos. 7,232,806; 7,078,196 and 7,056,704).

Posttranscriptional regulation of gene expression plays an especially important role in the survival of mammalian cells exposed to adverse environmental conditions (Ron, et al., *Nature reviews* 8:519-529 (2007)). Control is accomplished by the downregulation of protein synthesis due to the phosphorylation of the alpha subunit of eukaryotic translation initiation factor 2 (Hershey, *Annu. Rev. Biochem.* 60:717-755 (1991)). In addition, recent evidence has indicated the existence of a separate, phospho-eIF2α independent, translation control pathway (McEwen, et al., *J. Biol. Chem.* 280:16925-16933 (2005); Tenson, et al., *Mol. Microbiol.* 59:1664-1677 (2006); Rocha, et al., *Food Add. Contam.* 22:369-378 (2005); Iordanov, et al., *J. Biol. Chem.* 273:15794-15803 (1998); Shifrin, et al., *J. Biol. Chem.* 274:13985-13992 (1999)).

In Tetrahymena thermophila, nutrient stress induces cleavage of the tRNA anticodon loop to produce RNA fragments derived from the 5' and 3' ends of most, if not all, tRNAs (Lee, et al., *J. Biol. Chem.* 280:42744-42749 (2005)). The 3' fragments of these tiRNAs lack the terminal CCA residues required for aminoacylation, suggesting that anticodon cleavage occurs following 3' end processing, but prior to CCA addition. In mammalian cells, analogous RNAs comprise a small subset of piwi-associated piRNAs suggesting that tRNA anticodon cleavage may be a widespread phenomenon that can lead to the assembly of specific RNP complexes (Brennecke, et al., *Cell* 128:1089-1103 (2007); Grivna, et al., *Proc. Nat'l Acad. Sci. USA* 103:13415-13420 (2006); Lau, et al., Science 313:363-367 (2006)).

SUMMARY OF THE INVENTION

The present invention is based upon the discovery that, in response to stress, cells cleave tRNAs in or near the anticodon loop to form fragments (referred to herein as "tiRNAs" or, depending on context, more simply as "RNAs") that inhibit the translation of all mRNA transcripts. Cells treated with tiRNAs were found to undergo apoptosis. Thus, locally delivered synthetic RNAs corresponding to tiRNAs can be used to kill cells for either scientific or therapeutic purposes.

In its first aspect, the invention is directed to a method of inhibiting protein synthesis or inducing apoptosis in a population of cells by administering an effective amount of an RNA molecule 18-35, and preferably 28-30, nucleotides in length. These RNAs must have a sequence that is at least 90% identical to a sequence found within the first 40 nucleotides at the 5' end of a human tRNA. The term "effective amount" or "therapeutically effective amount" refers to a sufficient amount of tiRNA to inhibit protein synthesis by at least 10% and/or induce apoptosis in at least 10% of the cells treated and preferably in or by 20, 40, 60 or 80%.

The RNA may be part of a solution, suspension, or emulsion in which it is present at a concentration of 1 ng/ml-100 µg/ml, and preferably at a concentration of 10 ng/ml-10 µg/ml. Cells should typically be contacted with 10 ng-1 mg (and preferably 1 µg-500 µg of the RNA per million cells) and may be found either in vitro, e.g., growing in culture, or in vivo. For example, the RNA may be used to treat benign or malignant tumors, abnormal growths (especially melanomas) on the skin of a subject or conditions such as macular degeneration in which normal cells grow excessively. Most preferably, the RNA molecule is at least 18 (and preferably 28-30)

nucleotides long and at least 90% (and preferably 100%) identical to a sequence in SEQ ID NO:1-SEQ ID NO:132 as shown in Table 1.

In another aspect, the invention is directed to a topical composition in the form of a solution, cream, lotion, suspension, emulsion or gel, comprising 0.0001-10 weight percent (and preferably 0.001-1 wt %) of an RNA molecule 18-35 (and preferably 28-30) nucleotides in length. The RNA should comprise a sequence at least 18 nucleotides long and be at least 90% identical to a sequence in SEQ ID NO:1-SEQ ID NO:132 as shown in Table 1 together with one or more excipients. The RNA should be present in the composition at a concentration of 1 ng/ml-100 µg/ml, and preferably 10 ng/ml-10 µg/ml. The topical composition will be useful in treating skin conditions characterized by abnormal cellular growth such a melanomas.

The invention also includes injectable pharmaceutical compositions comprising 0.0001-10 weight percent (wt %) of RNA molecules with the characteristics described above together with a sterile carrier. These compositions may be delivered to sites of virus infection or applied as a microbicide to prevent virus infection. The method will be especially effective with respect to the treatment or prevention of sexually transmitted diseases and viruses that infect the eye. Examples of specific viruses that are amenable to this approach include: herpes simplex virus type 1; herpes simplex virus type 2; human papillomavirus; human immunodeficiency virus; and human cytomegalovirus. In the case of sexually transmitted viruses (e.g., human immunodeficiency virus or human papillomavirus), RNA may be delivered by means of a contraceptive device. In the case of an eye infection, the RNA may be delivered using a solution in the form of eye drops. In addition, RNA may be directly injected into benign or malignant tumors to induce cellular apoptosis. In general, it is expected that 0.1-100 ml of the RNA pharmaceutical composition will be administered per gram of tumor.

DETAILED DESCRIPTION OF THE INVENTION

A. Making of tiRNAs

Methods for chemically synthesizing short strands of RNA are well known in the art (see e.g., Usman, et al., *J. Am. Chem. Soc.* 109:7845 (1987); Scaringe et al., *Nucl. Ac. Res.* 18:5433 (1990); Wincott et al., *Nucl. Ac. Res.* 23:2677 (1995); Wincott et al., *Methods Mol. Biol.* 74:59 (1997) Milligan, *Nucl. Ac. Res.* 21:8783 (1987), all of which are hereby incorporated by reference in their entirety) and make use of common nucleic acid protecting and coupling groups. Syntheses may be performed on commercial equipment designed for this purpose, e.g., a 394 Applied Biosystems, Inc. synthesizer, using protocols supplied by the manufacturer. Any of these methods or alternative methods known in the art may be used to make the RNA of the present invention.

B. Pharmaceutical Compositions

The RNAs may be administered to patients in a pharmaceutical composition comprising the nucleic acids along with a pharmaceutically acceptable carrier or excipient. Carriers may be any solvent, diluent, liquid or solid vehicle that is pharmaceutically acceptable and typically used in formulating drugs. Guidance concerning the making of pharmaceutical formulations can be obtained from standard works in the art (see, e.g., *Remington's Pharmaceutical Sciences*, 16$^{th}$ edition, E. W. Martin, Easton, Pa. (1980)). In addition, pharmaceutical compositions may contain any of the excipients that are commonly used in the art. Examples of carriers or excipients that may be present include, but are not limited to, sugars (e.g., lactose, glucose and sucrose); starches, such as corn starch or potato starch; cellulose and its derivatives (e.g., sodium carboxymethyl cellulose, ethyl cellulose, or cellulose acetate); malt; gelatin; talc; cocoa butter; oils (e.g., peanut oil, cottonseed oil, safflower oil, sesame oil, olive oil, corn oil, or soybean oil); glycols; buffering agents; saline; Ringer's solution; alcohols; lubricants; coloring agents; dispersing agents; coating agents; flavoring agents; preservatives; or antioxidants.

C. Route of Delivery

The invention is compatible with the delivery of RNAs by any route known in the art, including peroral, intravaginal, internal, rectal, nasal, lingual, transdermal, intravenous, intra-arterial, intramuscular, intraperitoneal, intracutaneous and subcutaneous routes. The most preferred route is either topically or by local injection. It will also be understood that the RNAs may be in any pharmaceutically acceptable form of including pharmaceutically acceptable salts Liquid dosage forms for oral or topical administration include, but are not limited to, pharmaceutically acceptable emulsions, microemulsions, solutions, suspensions, syrups, creams, ointments and elixirs. In addition to the active compounds, liquid dosage form may contain inert diluents commonly used in the art, such as, for example, water, or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethyl formamide, oils, glycerol, alcohols, polyethylene glycols, and fatty acid esters. Injectable preparations may be in the form of sterile, injectable aqueous or oleaginous suspensions. Examples of diluents or solvents that may be used include 1,3-butanediol, water, Ringer's solution and isotonic saline solutions. In addition, oils or fatty acids may be present.

Pharmaceutical compositions may be given to a patient in one or more unit dosage forms. A "unit dosage form" refers to a single drug administration entity, e.g., a single tablet, capsule or injection vial. The amount of RNA present should be at least the amount required to inhibit protein synthesis by 10% and/or induce apoptosis in 10% of cells with higher percentages being preferred. The exact dosages may be determined for individual tiRNAs using methods that are well known in the art of pharmacology and may be further adjusted by physicians on a case-by-case basis based upon clinical considerations.

D. Methods for Delivering tiRNAs to Cells

Protocols for delivering RNA to cells have been described in many references including: Akhtar, et al., *Trends Cell Biol.* 2:139 (1992); WO 94/02595; WO99/04819; WO93/23569; and WO99/05094. Methods for administered nucleic acids to cells include: encapsulation in liposomes; by iontophoresis; or by incorporation into other vehicles, such as hydrogels, cyclodextrins, biodegradable nanocapsules, and bioadhesive microspheres. Alternatively, tiRNA may be locally delivered by direct injection or by use of an infusion pump. For a review of drug delivery strategies see Ho et al., *Curr. Opin. Mol. Ther.* 1:336 (1999) and Groothuis, et al., *J. NeuroVirol.* 3:387 (1997)) All of these references are hereby incorporated by reference in their entirety and may be used in conjunction with the present invention.

E. Treatment Methods

Cells growing in vitro may be contacted by the tiRNAs described herein in order to help in the study of apoptosis. Preparations may also be applied topically to skin lesions, e.g., lesions associated with melanoma. The exact dosage will be determined using procedures well known in the art, balancing toxicity and therapeutic efficacy. Compounds may also be given to test animals to study their effect. In these cases, dosages are limited only by toxicity. It should also be recognized that inhibitory compounds may be administered as the sole active agents in a dosage form, or they may be combined with other drugs to improve overall effectiveness.

EXAMPLES

The present example demonstrates that mammalian cells subjected to arsenite-induced oxidative stress, heat shock, or UV-irradiation activate a tRNA-anticodon nuclease to produce tRNA-derived, stress-induced RNAs (tiRNAs). Synthetic tiRNAs corresponding to the 5', but not the 3', end of tRNA inhibit protein translation in both reticulocyte lysates and transfected cells. The production and activity of tiRNAs is inversely correlated with the phosphorylation of eIF2α, suggesting that tiRNAs are components of a phospho-eIF2α-independent stress response program.

A. Experimental Procedures

Cell Culture and Treatment

U2OS cells were cultured in Dulbecco's modified Eagle's medium (DMEM, Life Technologies) supplemented with 10% fetal calf serum (Sigma) and antibiotics (penicillin (100 U/ml) and streptomycin (100 µg/ml). Lipofectamine 2000 (Invitrogen) and Optimem medium (Life Technologies) were used for transfection of tiRNAs and siRNAs. Wild type (SS) and S51A knock-in (AA) mouse embryonic fibroblasts (MEFs), were cultured in DMEM with 10% fetal calf serum and antibiotics. For stress induction, various doses of sodium arsenite (Sigma) were added in medium. The cells were washed with PBS twice before UV irradiation (UV crosslinker FB-UVXL-1000 (FisherBiotech)). Heat shock was achieved by incubating cells in a 42° C. oven.

RNA Analysis

Total RNA was extracted by using Trizol (Invitrogen). RNA (10 µg per well) was analyzed using TBS-Urea Gels (Invitrogen) or 1.1% agarose/2% formaldehyde MOPS gels, transferred to Nytran Supercharge membranes (Schleicher and Schuell) and hybridized overnight at 50° with digoxigenin-labeled DNA probes in DIG Easy Hyb solution (Roche). After washing at 60° with 2×SSC/0.1% SDS (10 min) and 0.5×SSC/0.1% SDS (20 min, 2 times), the membranes were blocked in Blocking Reagent (Roche) for 30 min at room temperature, probed with alkaline phosphatase-labeled anti-digoxigenin antibody (Roche) for 30 min and washed for 30 min with 130 mM TrisHCl pH 7.5/100 mM NaCl/0.3% Tween-20. Signals were visualized with CDP-Star (Roche). Probes for Httn-Q82, 28S rRNA and 18S rRNA were generated from U20S cDNA by PCR using digoxigenin-labeled nucleotides (Roche) and primer pairs (S198/S199 (Httn-Q82), S217/S218 (28S rRNA) and S215/S216 (18S rRNA), respectively). DIG labeled probes for 5S rRNA, tRNA and tiRNA were prepared by using DIG Oligonucleotide 3'-End Labeling Kit, $2^{nd}$ Generation (Roche) according to the manufacturer's protocol.

In Vitro Translation Assays

Flexi Rabbit Reticulocyte Lysate System (Promega) was used for in vitro luciferase translation according to the manufacturer's protocol. TNT Quick Coupled Transcription/Translation System (Promega) was used for in vitro Httn-Q82 reporter plasmid according to the manufacturer's protocol. Translation reactions were performed in a total volume of 10 µl at 30° C. for 30 minutes for luciferase and 12.5 µl at 30° C. for 90 minutes for Httn-Q82. The in vitro translated protein product was detected by immunoblot.

Biotinylated $tiRNA^{Ala}$ Pull Down Assay

To enrich tiRNA-associated RNPs, biotinylated $tiRNA^{Ala}$ and a biotinylated control RNA were added to an in vitro translation mixture (Flexi Rabbit Reticulocyte Lysate System) with luciferase mRNA in a total volume of 20 µl at 30° C. for 30 minutes. The reactions were diluted by the addition of binding buffer (20 mM Hepes, pH 7.9, 300 mM NaCl, 10 mM $MgCl_2$, 0.3% TritonX) containing RNasin-Plus RNase Inhibitor (Promega), Halt protease inhibitor cocktail and Halt phosphatase inhibitor cocktail (Pierce). The biotinylated RNA bound molecules were captured by Streptavidine Magnetic Particles (Roche) for 30 minutes at room temperature. The particles were washed with 1 ml binding buffer 6 times, then 33% of the particles were re-suspended in 2× sample buffer for western blot and 66% of the particles were extracted using TRIzol for northern blot.

Sucrose Gradient Analysis

U2OS cells at ~90% confluence were treated with or without SA (500 µM) for 90 minutes. The conditioned cells were washed in Hanks' balanced salt solution containing 5 µg/ml cycloheximide, and then scrape harvested and centrifuged. Pellets were lysed in 1 ml of ice-cold lysis buffer (300 mM NaCl, 15 mM Tris (pH 7.4), 15 mM $MgCl_2$, 1% TritonX, 0.5 U/ml, 5 µg/ml cycloheximide, RNasin-Plus RNase Inhibitor, Halt protease inhibitor cocktail. The cell suspension was incubated at 4° for 10 minutes. The sample was subjected to microfuge centrifugation for 15 min at 14,000 rpm. The resulting supernatant was then layered onto preformed 10-50% linear sucrose gradients (made up in 300 mM NaCl, 15 mM Tris (pH 7.4), 15 mM $MgCl_2$, 5 µg/ml cycloheximide, 14 mM 2-mercaptoethanole) over a 60%-0.5-ml sucrose cushion in 11 ml tubes (Beckman). Centrifugation was performed at 35,000 rpm for 190 minutes (for polysome fraction collection) or 250 minutes (for monosome fraction collection) using a Beckman SW40Ti rotor. Gradients were eluted from the top using a Brandel elution system (Brandel, Gaithersburg, Md.). The eluate was continuously monitored at 254 nm using an ISCO UA5 UV monitor (ISCO, Lincoln, Nebr.). Fractions were collected from the top of the gradient. Total RNA was extracted from individual fractions, and 0.5 µg of RNA was resolved by TBS-Urea Gel (Invitrogen) or 1.1% agarose/2% formaldehyde MOPS gel for Northern blotting.

Metabolic Labeling

Control RNA, 5' or 3' $tiRNA^{Ala}$ were transfected into U2OS cells in 24 well plates and cultured for various times. The cells were incubated with labeling medium (D-MEM without L-glutamine, sodium pyruvate, L-methionine or L-cystine, Invitrogen (Invitrogen)) supplemented with 5% dialyzed Fetal Bovine Serum (HyClone)) for 30 minutes, replaced with fresh labeling medium containing 150–250 µCi of L-$^{35}$S methionine/well (EasyTag™ EXPRESS35S Protein Labeling Mix) and incubated for 30 minutes. After washing with PBS twice, cells were harvested in 400 µl lysis buffer (2% SDS/20 mM Hepes, pH=7.4), sonicated, and the protein was precipitated by addition of 60% acetone. The proteins were re-suspended in lysis buffer and 10 µl of each sample in Ecoscint H (National Diagnostics) was counted using a liquid scintillation counter (Beckman, LS5801). Protein concentration was determined by Protein Assay BCA Protein Assay kit (PIERCE).

TUNEL Staining

U2OS cells grown on coverslips were transfected with control RNA, 5' or 3' tiRNA$^{Ala}$ for 12 hours using lipofectamine. TUNEL assay was performed by using ApopTag Fluorescein Direct In Situ Apoptosis Detection Kit (Chemicon) according to the manufacture's instruction followed by counter staining with Hoechst 33258. Cells were visualized using a Nikon Eclipse 800 microscope, and images were digitally captured using a CCD-SPOT RT digital camera and compiled using Adobe® Photoshop® software (v6.0).

B. Results and Discussion

Extracts prepared from human U2OS cells exposed to arsenite-induced oxidative stress, heat shock, or UV-irradiation were separated on a denaturing gel and developed with SYBR Gold to visualize stress-induced small RNAs. Northern blotting using cDNA probes complementary to the 5' end of tRNA$^{Met}$ and the 5' and 3' ends of various tRNAs revealed that these stress-induced RNAs are produced by tRNA cleavage. The size of these fragments requires that cleavage occur, as in Tetrahymena, in or near the anticodon loop. tiRNAs are rapidly induced (within 20 minutes) in response to arsenite-mediated oxidative stress and persist for at least 11 hours in cells allowed to recover from stress. The phosphorylation and dephosphorylation of eIF2α over this time course provided a marker of stress and recovery from stress. Arsenite-induced tiRNAs are observed in several different primate cell lines, indicating that this phenomenon is widespread in mammalian cells.

To determine the potential for tiRNAs to mediate phospho-eIF2α-independent translational arrest, we compared their induction in mouse embryo fibroblasts (MEFs) derived from wild type or eIF2α (S51A) mutant mice (Scheuner, et al., *Mol Cell* 7:1165-1176 (2001)). The expression of mature tRNA$^{Met}$ is similar in wild type (wt) and mutant (mut) cells in the absence or presence of arsenite (SA). In contrast, the induction of tiRNA$^{Met}$ is significantly greater in mutant cells, compared to wild type cells, indicating that phospho-eIF2α is not required for, and may inhibit, tiRNA production. This conclusion is supported by an enhanced production of tiRNAs in U2OS cells treated with control or heme-regulated initiation factor 2-α kinase (HRI)-specific siRNAs. Knock down of HRI, the eIF2α kinase activated by arsenite, increases the arsenite-induced production of tiRNAs. Taken together, these results indicate that stress-induced induction of tiRNAs does not require phospho-eIF2α. Moreover, phospho-eIF2α appears to suppress the induction of tiRNA.

We hypothesized that tiRNAs may inhibit translation by interfering with some aspect of tRNA function. Endogenous tiRNAs from arsenite-treated U2OS cells were gel-purified to enrich for small RNA populations including 5' and 3' tRNA fragments. These heterogeneous populations of small RNA were found to modestly inhibit the translation of luceriferase transcripts in reticulocyte lysates. To determine whether small RNAs corresponding to specific 5' or 3' tRNA fragments also suppress protein translation, we added synthetic tiRNAs (sequences corresponding to piwi-associated tRNA fragments) to reticulocyte lysates and quantified the synthesis of the luciferase reporter protein. Synthetic 5' tiRNA$^{Ala}$, but not 3' tiRNA$^{Ala}$, was found to inhibit protein translation in a dose dependent manner. The potency of 5' tiRNAs derived from different tRNAs differs reproducibly, with a rank order: 5' tiRNA$^{Ala}$>5' tiRNA$^{Pro}$>5' tiRNA$^{Gly}$>5' tiRNA$^{Gln}$. In a mixed transcription/translation system, synthetic 5' tiRNAs corresponding to gln, val, and met tRNAs were found to similarly inhibit the production of huntingtin protein without affecting huntingtin mRNA. The ability of 5' tiRNA$^{Val}$ to inhibit the translation of huntingtin, a protein that lacks valine residues, reveals that translational repression is codon independent.

Separation of extracts from U2OS cells cultured in the absence (−) or presence (SA) of arsenite over sucrose gradients showed that tiRNAs migrate near the top of the gradient and are found in fractions containing 40S, but not 60S ribosomal subunits. To determine whether tiRNA$^{Ala}$ can bind 40S ribosomal subunits, we compared the ability of biotinylated 5' tiRNA$^{Ala}$ and a biotinylated stem loop control RNA to pull down 18S ribosomal RNA from reticulocyte lysates. It was found that biotinylated 5'tiRNA$^{Ala}$, but not biotinylated stem loop control RNA, pulls down 18S rRNA, consistent with a specific interaction with the small ribosomal subunit.

Transfection of synthetic 5', but not 3', tiRNA$^{Ala}$ into U2OS cells induces a dose- and time-dependent inhibition of global protein synthesis. Moreover, synthetic 5', but not 3', tiRNA$^{Ala}$ inhibits global protein synthesis in both wild type and S51A mutant MEFs, indicating that inhibition of protein synthesis does not require phosphorylation of eIF2α. In both U2OS cells and MEFs, transfection of 5', but not 3', tiRNA$^{Ala}$ induces obvious toxicity (i.e., rounding up and blebbing) after approximately 9 hours. TUNEL staining showed that U2OS cells accumulate DNA strand breaks consistent with the onset of apoptotic cell death. Thus, both 5' tiRNA$^{Ala}$ and phospho-eIF2α inhibit protein synthesis and induce apoptosis in human cells.

Our results suggest that a stress-activated ribonuclease targets the anticodon loop of tRNAs to produce regulators of protein translation in mammalian cells. It is possible that intact tRNAs with nicked anticodon loops are an active component of this stress pathway. However, the findings that piwi proteins associate with both 5' and 3' tiRNAs, together with the ability of synthetic 5', but not 3', tiRNAs to inhibit protein translation and induce apoptosis, supports a role for processed tRNA fragments in this pathway.

Stress-induced phosphorylation of eIF2α inhibits translation initiation and triggers apoptotic cell death (Srivastava, et al., *J. Biol. Chem.* 273:2416-2423 (1998)). In viruses that replicate via dsRNA intermediates, PKR-induced phosphorylation of eIF2α triggers global inhibition of protein synthesis. These viruses counter the PKR/eIF2α translation control pathway by inactivating PKR or activating an eIF2α phosphatase (Garcia, et al., *Biochimie* 89:799-811 (2007)). The results described above suggest that stress-induced tRNA cleavage may provide a phospho-eIF2α independent pathway that inhibits protein synthesis and induces apoptosis.

TABLE 1

5' PiRNA Sequences

| tiRNA Homology | PiRNA Sequence | SEQ ID NO. | Reference |
|---|---|---|---|
| Ala tRNA | gggggguguagcucagugguagagcgcgugcuu | SEQ ID NO: 1 | *Homo sapiens* piRNA piR-36256 |
| | gggggguguagcucagugguagagcgcgugcu | SEQ ID NO: 2 | *Homo sapiens* piRNA piR-36255 |
| | ggggggguguagcucagugguagagcgcgugcu | SEQ ID NO: 3 | *Homo sapiens* piRNA piR-36243 |
| | gggggguguagcucagugguagagcgcgugc | SEQ ID NO: 4 | *Homo sapiens* piRNA piR-36254 |
| | ggggggguguagcucagugguagagcgcgugc | SEQ ID NO: 5 | *Homo sapiens* piRNA piR-36242 |
| | gggggunuagcucagugguagagcgcgugcuu | SEQ ID NO: 6 | *Homo sapiens* piRNA piR-36258 |
| | gggggguguagcucagugguagagcgcgug | SEQ ID NO: 7 | *Homo sapiens* piRNA piR-36253 |
| | guguagcucagugguagagcgcgugcuucgc | SEQ ID NO: 8 | *Homo sapiens* piRNA piR-36685 |
| | ggggunuagcucagugguagagcgcgugcuu | SEQ ID NO: 9 | *Homo sapiens* piRNA piR-36272 |
| | ggggggunuagcucagugguagagcgcgugcu | SEQ ID NO: 10 | *Homo sapiens* piRNA piR-36244 |
| | gggggguagcucaggguagagagcgcgugcuu | SEQ ID NO: 11 | *Homo sapiens* piRNA piR-36270 |
| | gggggunuagcucagugguagagcgcgugc | SEQ ID NO: 12 | *Homo sapiens* piRNA piR-36257 |
| | gggggguguagcucagugguagagagcgugcu | SEQ ID NO: 13 | *Homo sapiens* piRNA piR-36252 |
| | gggggauguagcucagugguagagcgcaugcu | SEQ ID NO: 14 | *Homo sapiens* piRNA piR-36225 |
| | gggggauuagcucaaaugguagagcgcucg | SEQ ID NO: 15 | *Homo sapiens* piRNA piR-36241 |
| | gggggaunuagcucagugguagagcgcaugcu | SEQ ID NO: 16 | *Homo sapiens* piRNA piR-36229 |
| Arg tRNA | ggcucuguugcgcaauggauagcgcau | SEQ ID NO: 17 | *Homo sapiens* piRNA piR-36082 |
| Asp tRNA | uccucauuaguauaguggguga guauccc | SEQ ID NO: 18 | *Homo sapiens* piRNA piR-44312 |
| Cys tRNA | gggggguauagcucagugguagagcauuuga | SEQ ID NO: 19 | *Homo sapiens* piRNA piR-36249 |
| | gggggguauagcucagugguagagcauuug | SEQ ID NO: 20 | *Homo sapiens* piRNA piR-36248 |
| | gggggguauagcucagugguagagcauuu | SEQ ID NO: 21 | *Homo sapiens* piRNA piR-36247 |
| | gggggguauagcucagugggguagagcau | SEQ ID NO: 22 | *Homo sapiens* piRNA piR-36246 |
| | gggggguauaacucagugguagagcauuuga | SEQ ID NO: 23 | *Homo sapiens* piRNA piR-36251 |
| Gln tRNA | gguuccauggguguaaugguuagcacucug | SEQ ID NO: 24 | *Homo sapiens* piRNA piR-36378 |
| Gly tRNA | uugguggguucaguggguagaauucucgccugcc | SEQ ID NO: 25 | *Homo sapiens* piRNA piR-61648 |
| | uugguggguucaguggguagaauucucgccugc | SEQ ID NO: 26 | *Homo sapiens* piRNA piR-61647 |
| | uugguggguucaguggguagaauucucgccug | SEQ ID NO: 27 | *Homo sapiens* piRNA piR-61646 |
| | uggugguucagugguagaauucucgccug | SEQ ID NO: 28 | *Homo sapiens* piRNA piR-57498 |
| | auugguggguucaguggguagaauucucgccug | SEQ ID NO: 29 | *Homo sapiens* piRNA piR-31925 |
| | uugguggguucaguggguagaauucucgccu | SEQ ID NO: 30 | *Homo sapiens* piRNA piR-61645 |
| | ggcauugguggguucaguggguagaauucucgc | SEQ ID NO: 31 | *Homo sapiens* piRNA piR-35982 |
| | auugguggguucaguggguagaauucucgcc | SEQ ID NO: 32 | *Homo sapiens* piRNA piR-31924 |
| | agcauugguggguucaguggguagaauucucgc | SEQ ID NO: 33 | *Homo sapiens* piRNA piR-31068 |
| | cauugguggguucaguggguagaauucucgc | SEQ ID NO: 34 | *Homo sapiens* piRNA piR-32679 |
| | gggaggcccggguucguuucccggccaaugca | SEQ ID NO: 35 | *Homo sapiens* piRNA piR-36173 |
| | gcauugguggguucaguggguagaauucucac | SEQ ID NO: 36 | *Homo sapiens* piRNA piR-35284 |
| | cgggaggcccggguucgguucccggccaaugc | SEQ ID NO: 37 | *Homo sapiens* piRNA piR-33486 |
| | uugguggguucaguggguagaauucucgc | SEQ ID NO: 38 | *Homo sapiens* piRNA piR-61644 |
| | gacauugguggguucaguggguagaauucu | SEQ ID NO: 39 | *Homo sapiens* piRNA piR-34358 |
| | ugguucaguggguagaauucucgccucc | SEQ ID NO: 40 | *Homo sapiens* piRNA piR-57660 |
| | gcauugguauaguggguaucaugcaaga | SEQ ID NO: 41 | *Homo sapiens* piRNA piR-35280 |
| | agcguugguggguauaguggugagcauagcugc | SEQ ID NO: 42 | *Homo sapiens* piRNA piR-31143 |
| His tRNA | ggccgugaucguauagugguuaguacucug | SEQ ID NO: 43 | *Homo sapiens* piRNA piR-36041 |
| | ucgcugaucguauagugguuaguacucug | SEQ ID NO: 44 | *Homo sapiens* piRNA piR-44984 |
| | ggccgugaucguauagugguuaguacuc | SEQ ID NO: 45 | *Homo sapiens* piRNA piR-36040 |
| | aggccgugaucguauagugguuaguacuc | SEQ ID NO: 46 | *Homo sapiens* piRNA piR-31355 |
| | ggccgugaucguauagugguuaguacu | SEQ ID NO: 47 | *Homo sapiens* piRNA piR-36039 |
| | ggccgugaucguauagugguua guac | SEQ ID NO: 48 | *Homo sapiens* piRNA piR-36038 |
| Ile tRNA | ggccgguuagcucaguugguuagagc | SEQ ID NO: 49 | *Homo sapiens* piRNA piR-36037 |
| | ggccguagcucagugguucagagc | SEQ ID NO: 50 | *Homo sapiens* piRNA piR-36036 |
| | ggccgguuagcucagugguaagagcuuggu | SEQ ID NO: 51 | *Homo sapiens* piRNA piR-36035 |
| | ggggcggccgguuagcucagugguaagagc | SEQ ID NO: 52 | *Homo sapiens* piRNA piR-36235 |
| | ggccgguuagcucagugguaagagc | SEQ ID NO: 53 | *Homo sapiens* piRNA piR-36034 |
| Leu tRNA | gguaguguggccgagcggucuaaggc | SEQ ID NO: 54 | *Homo sapiens* piRNA piR-36318 |
| | guagucguggccgagugguuaaggcuaugga | SEQ ID NO: 55 | *Homo sapiens* piRNA piR-36441 |
| | gacgaggguggccgagugguuaaggcuauggau | SEQ ID NO: 56 | *Homo sapiens* piRNA piR-34444 |
| | gacgaggguggccgagugguuaaggcuauggac | SEQ ID NO: 57 | *Homo sapiens* piRNA piR-34443 |
| | gacgaggguggccgagugguuaaggcuaugga | SEQ ID NO: 58 | *Homo sapiens* piRNA piR-34442 |
| | gacgaggguggccgagugguuaaggcuaugg | SEQ ID NO: 59 | *Homo sapiens* piRNA piR-34441 |
| | gacgaggguggccgagugguuaaggcaaugga | SEQ ID NO: 60 | *Homo sapiens* piRNA piR-34440 |
| | gacgaggguggccgagugguuaaggcaaugg | SEQ ID NO: 61 | *Homo sapiens* piRNA piR-34439 |
| | uguagucguggccgagu gguuaaggc | SEQ ID NO: 62 | *Homo sapiens* piRNA piR-57942 |

TABLE 1-continued

5' PiRNA Sequences

| tiRNA Homology | PiRNA Sequence | SEQ ID NO. | Reference |
|---|---|---|---|
| Lys tRNA | gccuggauagcucaguugguagagcaucaga | SEQ ID NO: 63 | Homo sapiens piRNA piR-35463 |
| | gccuggauagcucaguugguagagcauca | SEQ ID NO: 64 | Homo sapiens piRNA piR-35462 |
| | gccugggauagcucagucgguagagcaucagac | SEQ ID NO: 65 | Homo sapiens piRNA piR-35469 |
| | gccugggauagcucagucgguagagcaucaga | SEQ ID NO: 66 | Homo sapiens piRNA piR-35468 |
| | gccugggauagcucagucgguagagcaucag | SEQ ID NO: 67 | Homo sapiens piRNA piR-35467 |
| Met tRNA | gcagaguggcgcagcggaagcgugcugggccc | SEQ ID NO: 68 | Homo sapiens piRNA piR-35176 |
| | ggcagaguggcgcagcggaagcgugcugggcc | SEQ ID NO: 69 | Homo sapiens piRNA piR-35952 |
| | gcagaguggcgcagcggaagcgugcugg | SEQ ID NO: 70 | Homo sapiens piRNA piR-35175 |
| | ugcagaguggcgcagcggaagcgugcugg | SEQ ID NO: 71 | Homo sapiens piRNA piR-50725 |
| | gcaguggcgcagcggaagcgugcugggcc | SEQ ID NO: 72 | Homo sapiens piRNA piR-35229 |
| | gcagaguggcgcagcggaagcgugcug | SEQ ID NO: 73 | Homo sapiens piRNA piR-35174 |
| | cgcagagucgcgcagcggaagcgugcugggcc | SEQ ID NO: 74 | Homo sapiens piRNA piR-33387 |
| | cagagucgcgcagcggaagcgugcugggccc | SEQ ID NO: 75 | Homo sapiens piRNA piR-32374 |
| | agaguugcgcagcggaagcgugcugggccca | SEQ ID NO: 76 | Homo sapiens piRNA piR-30961 |
| | gagauagcagaguggcgcagcggaagc | SEQ ID NO: 77 | Homo sapiens piRNA piR-30926 |
| Pro tRNA | ggcucguuggucuaggggauaugauucucgg | SEQ ID NO: 78 | Homo sapiens piRNA piR-36074 |
| | aggcucguuggucuagugguaugauucucg | SEQ ID NO: 79 | Homo sapiens piRNA piR-31368 |
| SeC tRNA | gcccggaugauccucaguggucuggggugc | SEQ ID NO: 80 | Homo sapiens piRNA piR-35407 |
| Ser tRNA | uguagucguggccgaguggguuaaggc | SEQ ID NO: 81 | Homo sapiens piRNA piR-57942 |
| | gacgagguggccgaguggguuaaggcuauggac | SEQ ID NO: 82 | Homo sapiens piRNA piR-34443 |
| | gacgagguggccgaguggguuaaggcuauggau | SEQ ID NO: 83 | Homo sapiens piRNA piR-34444 |
| | gacgagguggccgaguggguuaaggcuaugga | SEQ ID NO: 84 | Homo sapiens piRNA piR-34442 |
| | gacgagguggccgaguggguuaaggcaaugga | SEQ ID NO: 85 | Homo sapiens piRNA piR-34440 |
| | gacgagguggccgaguggguuaaggcuaugg | SEQ ID NO: 86 | Homo sapiens piRNA piR-34441 |
| | gacgagguggccgaguggguuaaggcaaugg | SEQ ID NO: 87 | Homo sapiens piRNA piR-34439 |
| Sup tRNA | gccuggauagcucaguugguagagcaucaga | SEQ ID NO: 88 | Homo sapiens piRNA piR-35463 |
| | gccuggauagcucaguugguagagcauca | SEQ ID NO: 89 | Homo sapiens piRNA piR-35462 |
| Thr tRNA | ggcagaguggcgcagcggaagcgugcugggcc | SEQ ID NO: 90 | Homo sapiens piRNA piR-35952 |
| | gcagaguggcgcagcggaagcgugcugggccc | SEQ ID NO: 91 | Homo sapiens piRNA piR-35176 |
| | gcagaguggcgcagcggaagcgugcugg | SEQ ID NO: 92 | Homo sapiens piRNA piR-35175 |
| | cggaagcgugcugggcccauaacccaga | SEQ ID NO: 93 | Homo sapiens piRNA piR-33437 |
| | ugcagaguggcgcagcggaagcgugcugg | SEQ ID NO: 94 | Homo sapiens piRNA piR-50725 |
| | gcaguggcgcagcggaagcgugcugggcc | SEQ ID NO: 95 | Homo sapiens piRNA piR-35229 |
| | gcagaguggcgcagcggaagcgugcug | SEQ ID NO: 96 | Homo sapiens piRNA piR-35174 |
| | cgcagagucgcgcagcggaagcgugcugggcc | SEQ ID NO: 97 | Homo sapiens piRNA piR-33387 |
| | cagagucgcgcagcggaagcgugcugggccc | SEQ ID NO: 98 | Homo sapiens piRNA piR-32374 |
| | agaguugcgcagcggaagcgugcugggccca | SEQ ID NO: 99 | Homo sapiens piRNA piR-30961 |
| Tyr tRNA | gccuggauagcucaguugguagagcaucaga | SEQ ID NO: 100 | Homo sapiens piRNA piR-35463 |
| | gccuggauagcucaguugguagagcauca | SEQ ID NO: 101 | Homo sapiens piRNA piR-35462 |
| Val tRNA | uuccguaguguagugguuaucacguucgccuc | SEQ ID NO: 102 | Homo sapiens piRNA piR-60577 |
| | uuccguaguguagugguuaucacguucgcc | SEQ ID NO: 103 | Homo sapiens piRNA piR-60576 |
| | uccguaguguagugguuaucacguucgccuga | SEQ ID NO: 104 | Homo sapiens piRNA piR-43996 |
| | uccguaguguagugguuaucacguucgccug | SEQ ID NO: 105 | Homo sapiens piRNA piR-43995 |
| | uccguaguguagugguuaucacguucgccuca | SEQ ID NO: 106 | Homo sapiens piRNA piR-43994 |
| | uccguaguguagugguuaucacguucgccu | SEQ ID NO: 107 | Homo sapiens piRNA piR-43993 |
| | guuuccguaguguaguggucaucacguucgcc | SEQ ID NO: 108 | Homo sapiens piRNA piR-36743 |
| | ccguaguguagugguuaucacguucgcc | SEQ ID NO: 109 | Homo sapiens piRNA piR-33164 |
| | guuccguaguguaguggucaucacguucgc | SEQ ID NO: 110 | Homo sapiens piRNA piR-36742 |
| | cguaguguagugguuaucacguucgcc | SEQ ID NO: 111 | Homo sapiens piRNA piR-33520 |
| | uccguaguguaguggguuaucacuuucgccu | SEQ ID NO: 112 | Homo sapiens piRNA piR-43997 |
| | uccguaguguacuggguuaucacguucgccug | SEQ ID NO: 113 | Homo sapiens piRNA piR-43992 |
| | cguaguguaguggucaucacguucgccu | SEQ ID NO: 114 | Homo sapiens piRNA piR-33519 |
| | gggggguguagcucaguggguagagcgcugcuu | SEQ ID NO: 115 | Homo sapiens piRNA piR-36256 |
| | gggggguguagcucaguggguagagcgcugcu | SEQ ID NO: 116 | Homo sapiens piRNA piR-36255 |
| | gggggguguagcucaguggguagagcgcugc | SEQ ID NO: 117 | Homo sapiens piRNA piR-36254 |
| | gggggguguagcucaguggguagagcgcug | SEQ ID NO: 118 | Homo sapiens piRNA piR-36253 |
| | gggggguguagcucaguggguagagcgcgucu | SEQ ID NO: 119 | Homo sapiens piRNA piR-36243 |
| | uuggugguucaguggguagaauucucgccugc | SEQ ID NO: 120 | Homo sapiens piRNA piR-61648 |
| | uuggugguucaguggguagaauucucgccugc | SEQ ID NO: 121 | Homo sapiens piRNA piR-61647 |
| | uuggugguucaguggguagaauucucgccug | SEQ ID NO: 122 | Homo sapiens piRNA piR-61646 |
| | uuggugguucaguggguagaauucucgccu | SEQ ID NO: 123 | Homo sapiens piRNA piR-61645 |
| | uugguguuucaguggguagaauucucgccug | SEQ ID NO: 124 | Homo sapiens piRNA piR-57498 |
| | auuggugguucaguggguagaauucucgccugc | SEQ ID NO: 125 | Homo sapiens piRNA piR-31925 |
| | auuggugguucaguggguagaauucucgcc | SEQ ID NO: 126 | Homo sapiens piRNA piR-31924 |
| | ggcauuggugguucaguggguagaauucucgc | SEQ ID NO: 127 | Homo sapiens piRNA piR-35982 |
| | uugguguuucaguggguagaauucucgc | SEQ ID NO: 128 | Homo sapiens piRNA piR-61644 |
| | ugguucaguggguagaauucucgccucc | SEQ ID NO: 129 | Homo sapiens piRNA piR-57660 |

TABLE 1-continued

5' PiRNA Sequences

| tiRNA Homology | PiRNA Sequence | SEQ ID NO. | Reference |
|---|---|---|---|
| | cauuggugguucagugguagaauucucgc | SEQ ID NO: 130 | *Homo sapiens* piRNA piR-32679 |
| | agcauuggugguucagugguagaauucucgc | SEQ ID NO: 131 | *Homo sapiens* piRNA piR-31068 |
| | gcauuggugguucagugguagaauucucac | SEQ ID NO: 132 | *Homo sapiens* piRNA piR-35284 |

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of inducing apoptosis or inhibiting protein synthesis in a population of cells, comprising administering to said cells an effective amount of an RNA molecule 18-35 nucleotides in length, wherein said RNA molecule has a sequence that is at least 90% identical to a sequence found within the first 40 nucleotides at the 5' end of a human stress-induced transfer RNA (tiRNA).

2. The method of claim 1, wherein said RNA is selected from the group consisting of: SEQ ID NO:1-SEQ ID NO:132.

3. The method of claim 2, wherein said RNA is present as part of a solution, suspension or emulsion at a concentration of 10 ng/ml-10 µg/ml.

4. The method of claim 2, wherein said cells are contacted with 1 µg-500 µg of RNA per million cells.

5. The method of claim 2, wherein said population of cells are in vitro.

6. The method of claim 2, wherein said population of cells are part of a benign or malignant tumor, an abnormal growth on the skin of a subject or are cells that are otherwise growing in vivo in an abnormally excessive manner.

7. A therapeutic method comprising administering to a patient an effective amount of a pharmaceutical composition comprising an RNA molecule 18-35 nucleotides in length, wherein said RNA molecule has a sequence that is at least 90% identical to a sequence found within the first 40 nucleotides at the 5' end of a human stress-induced transfer RNA (tiRNA).

8. The therapeutic method of claim 7, wherein said pharmaceutical composition is in the form of a solution, cream, lotion, suspension, emulsion or gel, and said patient is treated for an abnormal dermatological growth by topically applying said composition.

9. The therapeutic method of claim 8, wherein said abnormal dermatological growth is a melanoma and wherein said patient is administered an RNA selected from the group consisting of: SEQ ID NO:1-SEQ ID NO:132.

10. The therapeutic method of claim 7, wherein said pharmaceutical composition is in the form of an injectable composition and said patient is treated for a benign or malignant tumor by injecting said tumor with said composition.

11. The therapeutic method of claim 10, wherein said benign or malignant tumor is injected with 0.1-100 ml of said pharmaceutical composition per gram of tumor and wherein said patient is administered an RNA selected from the group consisting of: SEQ ID NO:1-SEQ ID NO:132.

12. The therapeutic method of claim 7, wherein said therapeutic method comprises treating viral infection in a population of eukaryotic cells, by administering said pharmaceutical composition to said cells.

13. The therapeutic method of claim 12, wherein said viral infection is caused by a sexually transmitted virus or a virus that infects the eye of patients and wherein said RNA is selected from the group consisting of: SEQ ID NO:1-SEQ ID NO:132.

14. The therapeutic method of claim 12, wherein said viral infection is caused by a virus selected from the group consisting of: herpes simplex virus type 1; herpes simplex virus type 2; human papillomavirus; human immunodeficiency virus; and human cytomegalovirus and wherein said RNA is selected from the group consisting of: SEQ ID NO:1-SEQ ID NO:132.

15. The therapeutic method of claim 12, wherein said RNA is part of a solution, suspension, emulsion, cream, lotion, ointment, or gel and is present at a concentration of 1 ng/ml-100 µg/ml.

16. The therapeutic method of claim 12, wherein said cells are contacted with 1 µg-500 µg of RNA per million cells.

17. The method of claim 2, wherein said RNA molecule has a sequence consisting of the sequence of any one of SEQ ID NO:17-SEQ ID NO:132.

18. The method of claim 2, wherein said RNA molecule has a sequence consisting of the sequence of any one of SEQ ID NO:1-SEQ ID NO:16.

19. The therapeutic method of claim 8, wherein said RNA molecule has a sequence consisting of the sequence of any one of SEQ ID NO:17-SEQ ID NO:132.

20. The therapeutic method of claim 8, wherein said RNA molecule has a sequence consisting of the sequence of any one of SEQ ID NO:1-SEQ ID NO:16.

* * * * *

```
                            SEQUENCE LISTING

<160> NUMBER OF SEQ ID NOS: 132

<210> SEQ ID NO 1
<211> LENGTH: 32
<212> TYPE: RNA
<213> ORGANISM: Homo sapiens

<400> SEQUENCE: 1 gggggguguag cucaguggua gagcgcgugc uu                                    32

<210> SEQ ID NO 2
<211> LENGTH: 31
<212> TYPE: RNA
<213> ORGANISM: Homo sapiens

<400> SEQUENCE: 2 gggggguguag cucaguggua gagcgcgugc u                                     31

<210> SEQ ID NO 3
<211> LENGTH: 32
<212> TYPE: RNA
<213> ORGANISM: Homo sapiens

<400> SEQUENCE: 3 gggggugugua gcucaguggu agagcgcgug cu                                    32

<210> SEQ ID NO 4
<211> LENGTH: 30
<212> TYPE: RNA
<213> ORGANISM: Homo sapiens

<400> SEQUENCE: 4 gggggguguag cucaguggua gagcgcgugc                                       30

<210> SEQ ID NO 5
<211> LENGTH: 31
<212> TYPE: RNA
<213> ORGANISM: Homo sapiens

<400> SEQUENCE: 5 gggggugugua gcucaguggu agagcgcgug c                                     31

<210> SEQ ID NO 6
<211> LENGTH: 32
<212> TYPE: RNA
<213> ORGANISM: Homo sapiens
<220> FEATURE:
<221> NAME/KEY: misc_feature
<222> LOCATION: (7)..(7)
```

<223> OTHER INFORMATION: n is a, c, g, or u

<400> SEQUENCE: 6
gggggunuag cucaguggua gagcgcgugc uu                       32

<210> SEQ ID NO 7
<211> LENGTH: 29
<212> TYPE: RNA
<213> ORGANISM: Homo sapiens

<400> SEQUENCE: 7 gggggguag cucaguggua gagcgcgug                            29

<210> SEQ ID NO 8
<211> LENGTH: 31
<212> TYPE: RNA
<213> ORGANISM: Homo sapiens

<400> SEQUENCE: 8
guguagcuca gugguagagc gcgugcuucg c                        31

<210> SEQ ID NO 9
<211> LENGTH: 31
<212> TYPE: RNA
<213> ORGANISM: Homo sapiens
<220> FEATURE:
<221> NAME/KEY: misc_feature
<222> LOCATION: (6)..(6)
<223> OTHER INFORMATION: n is a, c, g, or u

<400> SEQUENCE: 9
ggggunuagc ucaggguag agcgcgugcu u                         31

<210> SEQ ID NO 10
<211> LENGTH: 32
<212> TYPE: RNA
<213> ORGANISM: Homo sapiens
<220> FEATURE:
<221> NAME/KEY: misc_feature
<222> LOCATION: (8)..(8)
<223> OTHER INFORMATION: n is a, c, g, or u

<400> SEQUENCE: 10 gggggunua gcucaguggu agagcgcgug cu                        32

<210> SEQ ID NO 11
<211> LENGTH: 31
<212> TYPE: RNA
<213> ORGANISM: Homo sapiens

<400> SEQUENCE: 11
gggguguagc ucaggguag agagcgugcu u                         31

<210> SEQ ID NO 12
<211> LENGTH: 30
<212> TYPE: RNA
<213> ORGANISM: Homo sapiens
<220> FEATURE:
<221> NAME/KEY: misc_feature
<222> LOCATION: (7)..(7)
<223> OTHER INFORMATION: n is a, c, g, or u

<400> SEQUENCE: 12 ggggunuag cucaguggua gagcgcgugc                           30

<210> SEQ ID NO 13

-continued

```
<211> LENGTH: 31
<212> TYPE: RNA
<213> ORGANISM: Homo sapiens

<400> SEQUENCE: 13 gggggguguag cucaguggua gagagcgugc u                                    31

<210> SEQ ID NO 14
<211> LENGTH: 31
<212> TYPE: RNA
<213> ORGANISM: Homo sapiens

<400> SEQUENCE: 14
ggggauguag cucaguggua gagcgcaugc u                                     31

<210> SEQ ID NO 15
<211> LENGTH: 30
<212> TYPE: RNA
<213> ORGANISM: Homo sapiens

<400> SEQUENCE: 15
gggggauuag cucaaauggu agagcgcucg                                       30

<210> SEQ ID NO 16
<211> LENGTH: 31
<212> TYPE: RNA
<213> ORGANISM: Homo sapiens
<220> FEATURE:
<221> NAME/KEY: misc_feature
<222> LOCATION: (7)..(7)
<223> OTHER INFORMATION: n is a, c, g, or u

<400> SEQUENCE: 16
ggggaunuag cucaguggua gagcgcaugc u                                     31

<210> SEQ ID NO 17
<211> LENGTH: 27
<212> TYPE: RNA
<213> ORGANISM: Homo sapiens

<400> SEQUENCE: 17
ggcucuguug cgcaauggau agcgcau                                          27

<210> SEQ ID NO 18
<211> LENGTH: 28
<212> TYPE: RNA
<213> ORGANISM: Homo sapiens

<400> SEQUENCE: 18
uccucauuag uauaguggug aguauccc                                         28

<210> SEQ ID NO 19
<211> LENGTH: 30
<212> TYPE: RNA
<213> ORGANISM: Homo sapiens

<400> SEQUENCE: 19 gggguauag cucaguggua gagcauuuga                                        30

<210> SEQ ID NO 20
<211> LENGTH: 29
<212> TYPE: RNA
<213> ORGANISM: Homo sapiens

<400> SEQUENCE: 20
```

```
ggggguauag cucaguggua gagcauuug                                    29

<210> SEQ ID NO 21
<211> LENGTH: 28
<212> TYPE: RNA
<213> ORGANISM: Homo sapiens

<400> SEQUENCE: 21
ggggguauag cucaguggua gagcauuu                                     28

<210> SEQ ID NO 22
<211> LENGTH: 27
<212> TYPE: RNA
<213> ORGANISM: Homo sapiens

<400> SEQUENCE: 22
ggggguauag cucagugggu agagcau                                      27

<210> SEQ ID NO 23
<211> LENGTH: 30
<212> TYPE: RNA
<213> ORGANISM: Homo sapiens

<400> SEQUENCE: 23 gggggguaa cucaguggua gagcauuuga                                    30

<210> SEQ ID NO 24
<211> LENGTH: 29
<212> TYPE: RNA
<213> ORGANISM: Homo sapiens

<400> SEQUENCE: 24 gguccaugg uguaaugguu agcacucug                                     29

<210> SEQ ID NO 25
<211> LENGTH: 32
<212> TYPE: RNA
<213> ORGANISM: Homo sapiens

<400> SEQUENCE: 25
uuggugguuc aguguagaa uucucgccug cc                                 32

<210> SEQ ID NO 26
<211> LENGTH: 31
<212> TYPE: RNA
<213> ORGANISM: Homo sapiens

<400> SEQUENCE: 26
uuggugguuc aguguagaa uucucgccug c                                  31

<210> SEQ ID NO 27
<211> LENGTH: 30
<212> TYPE: RNA
<213> ORGANISM: Homo sapiens

<400> SEQUENCE: 27
uuggugguuc aguguagaa uucucgccug                                    30

<210> SEQ ID NO 28
<211> LENGTH: 29
<212> TYPE: RNA
<213> ORGANISM: Homo sapiens

<400> SEQUENCE: 28
uggugguuca guguagaau ucucgccug                                     29
```

```
<210> SEQ ID NO 29
<211> LENGTH: 31
<212> TYPE: RNA
<213> ORGANISM: Homo sapiens

<400> SEQUENCE: 29
auuggugguu cagugguaga auucucgccu g                              31

<210> SEQ ID NO 30
<211> LENGTH: 29
<212> TYPE: RNA
<213> ORGANISM: Homo sapiens

<400> SEQUENCE: 30
uuggugguuc agugguagaa uucucgccu                                 29

<210> SEQ ID NO 31
<211> LENGTH: 31
<212> TYPE: RNA
<213> ORGANISM: Homo sapiens

<400> SEQUENCE: 31
ggcauuggug guucaguggu agaauucucg c                              31

<210> SEQ ID NO 32
<211> LENGTH: 29
<212> TYPE: RNA
<213> ORGANISM: Homo sapiens

<400> SEQUENCE: 32
auuggugguu cagugguaga auucucgcc                                 29

<210> SEQ ID NO 33
<211> LENGTH: 31
<212> TYPE: RNA
<213> ORGANISM: Homo sapiens

<400> SEQUENCE: 33
agcauuggug guucaguggu agaauucucg c                              31

<210> SEQ ID NO 34
<211> LENGTH: 29
<212> TYPE: RNA
<213> ORGANISM: Homo sapiens

<400> SEQUENCE: 34
cauugguggu ucaguggua g aauucucgc                                29

<210> SEQ ID NO 35
<211> LENGTH: 32
<212> TYPE: RNA
<213> ORGANISM: Homo sapiens

<400> SEQUENCE: 35
gggaggcccg gguucguuuc ccggccaaug ca                             32

<210> SEQ ID NO 36
<211> LENGTH: 30
<212> TYPE: RNA
<213> ORGANISM: Homo sapiens

<400> SEQUENCE: 36
gcauuggugg uucaguggua gaauucucac                                30
```

```
<210> SEQ ID NO 37
<211> LENGTH: 32
<212> TYPE: RNA
<213> ORGANISM: Homo sapiens

<400> SEQUENCE: 37
cgggaggccc ggguucgguu cccggccaau gc                              32

<210> SEQ ID NO 38
<211> LENGTH: 27
<212> TYPE: RNA
<213> ORGANISM: Homo sapiens

<400> SEQUENCE: 38
uuggugguuc aggguagaa uucucgc                                     27

<210> SEQ ID NO 39
<211> LENGTH: 28
<212> TYPE: RNA
<213> ORGANISM: Homo sapiens

<400> SEQUENCE: 39 gacauggug guucaguggu agaauucu                                    28

<210> SEQ ID NO 40
<211> LENGTH: 27
<212> TYPE: RNA
<213> ORGANISM: Homo sapiens

<400> SEQUENCE: 40
ugguucagug guagaauucu cgccucc                                    27

<210> SEQ ID NO 41
<211> LENGTH: 27
<212> TYPE: RNA
<213> ORGANISM: Homo sapiens

<400> SEQUENCE: 41
gcauugguau agugguauca ugcaaga                                    27

<210> SEQ ID NO 42
<211> LENGTH: 32
<212> TYPE: RNA
<213> ORGANISM: Homo sapiens

<400> SEQUENCE: 42
agcguuggug guauaguggu gagcauagcu gc                              32

<210> SEQ ID NO 43
<211> LENGTH: 30
<212> TYPE: RNA
<213> ORGANISM: Homo sapiens

<400> SEQUENCE: 43
ggccgugauc guauaguggu uaguacucug                                 30

<210> SEQ ID NO 44
<211> LENGTH: 31
<212> TYPE: RNA
<213> ORGANISM: Homo sapiens

<400> SEQUENCE: 44
ucgccgugau cguauagugg uuaguacucu g                               31
```

```
<210> SEQ ID NO 45
<211> LENGTH: 28
<212> TYPE: RNA
<213> ORGANISM: Homo sapiens

<400> SEQUENCE: 45
ggccgugauc guauaguggu uaguacuc                                          28

<210> SEQ ID NO 46
<211> LENGTH: 29
<212> TYPE: RNA
<213> ORGANISM: Homo sapiens

<400> SEQUENCE: 46
aggccgugau cguauagugg uuaguacuc                                         29

<210> SEQ ID NO 47
<211> LENGTH: 27
<212> TYPE: RNA
<213> ORGANISM: Homo sapiens

<400> SEQUENCE: 47
ggccgugauc guauaguggu uaguacu                                           27

<210> SEQ ID NO 48
<211> LENGTH: 26
<212> TYPE: RNA
<213> ORGANISM: Homo sapiens

<400> SEQUENCE: 48
ggccgugauc guauaguggu uaguac                                            26

<210> SEQ ID NO 49
<211> LENGTH: 26
<212> TYPE: RNA
<213> ORGANISM: Homo sapiens

<400> SEQUENCE: 49
ggccgguuag cucaguuggu uagagc                                            26

<210> SEQ ID NO 50
<211> LENGTH: 26
<212> TYPE: RNA
<213> ORGANISM: Homo sapiens

<400> SEQUENCE: 50
ggccgguuag cucaguuggu cagagc                                            26

<210> SEQ ID NO 51
<211> LENGTH: 31
<212> TYPE: RNA
<213> ORGANISM: Homo sapiens

<400> SEQUENCE: 51
ggccgguuag cucaguuggu aagagcuugg u                                      31

<210> SEQ ID NO 52
<211> LENGTH: 31
<212> TYPE: RNA
<213> ORGANISM: Homo sapiens

<400> SEQUENCE: 52
ggggcggccg guuagcucag uugguaagag c                                      31
```

```
<210> SEQ ID NO 53
<211> LENGTH: 26
<212> TYPE: RNA
<213> ORGANISM: Homo sapiens

<400> SEQUENCE: 53
ggccgguuag cucaguuggu aagagc                                          26

<210> SEQ ID NO 54
<211> LENGTH: 26
<212> TYPE: RNA
<213> ORGANISM: Homo sapiens

<400> SEQUENCE: 54
gguagugugg ccgagcgguc uaaggc                                          26

<210> SEQ ID NO 55
<211> LENGTH: 31
<212> TYPE: RNA
<213> ORGANISM: Homo sapiens

<400> SEQUENCE: 55
guagucgugg ccgagugguu aaggcuaugg a                                    31

<210> SEQ ID NO 56
<211> LENGTH: 32
<212> TYPE: RNA
<213> ORGANISM: Homo sapiens

<400> SEQUENCE: 56
gacgaggugg ccgagugguu aaggcuaugg au                                   32

<210> SEQ ID NO 57
<211> LENGTH: 32
<212> TYPE: RNA
<213> ORGANISM: Homo sapiens

<400> SEQUENCE: 57
gacgaggugg ccgagugguu aaggcuaugg ac                                   32

<210> SEQ ID NO 58
<211> LENGTH: 31
<212> TYPE: RNA
<213> ORGANISM: Homo sapiens

<400> SEQUENCE: 58
gacgaggugg ccgagugguu aaggcuaugg a                                    31

<210> SEQ ID NO 59
<211> LENGTH: 30
<212> TYPE: RNA
<213> ORGANISM: Homo sapiens

<400> SEQUENCE: 59
gacgaggugg ccgagugguu aaggcuaugg                                      30

<210> SEQ ID NO 60
<211> LENGTH: 31
<212> TYPE: RNA
<213> ORGANISM: Homo sapiens

<400> SEQUENCE: 60
gacgaggugg ccgagugguu aaggcaaugg a                                    31
```

```
<210> SEQ ID NO 61
<211> LENGTH: 30
<212> TYPE: RNA
<213> ORGANISM: Homo sapiens

<400> SEQUENCE: 61
gacgaggugg ccgaguggeu aaggcaaugg                                    30

<210> SEQ ID NO 62
<211> LENGTH: 26
<212> TYPE: RNA
<213> ORGANISM: Homo sapiens

<400> SEQUENCE: 62
uguagucgug gccgaguggu uaaggc                                        26

<210> SEQ ID NO 63
<211> LENGTH: 31
<212> TYPE: RNA
<213> ORGANISM: Homo sapiens

<400> SEQUENCE: 63
gccuggauag cucaguuggu agagcaucag a                                  31

<210> SEQ ID NO 64
<211> LENGTH: 29
<212> TYPE: RNA
<213> ORGANISM: Homo sapiens

<400> SEQUENCE: 64
gccuggauag cucaguuggu agagcauca                                     29

<210> SEQ ID NO 65
<211> LENGTH: 32
<212> TYPE: RNA
<213> ORGANISM: Homo sapiens

<400> SEQUENCE: 65
gccuggguag cucagucggu agagcaucag ac                                 32

<210> SEQ ID NO 66
<211> LENGTH: 31
<212> TYPE: RNA
<213> ORGANISM: Homo sapiens

<400> SEQUENCE: 66
gccuggguag cucagucggu agagcaucag a                                  31

<210> SEQ ID NO 67
<211> LENGTH: 30
<212> TYPE: RNA
<213> ORGANISM: Homo sapiens

<400> SEQUENCE: 67
gccuggguag cucagucggu agagcaucag                                    30

<210> SEQ ID NO 68
<211> LENGTH: 32
<212> TYPE: RNA
<213> ORGANISM: Homo sapiens

<400> SEQUENCE: 68
gcagaguggc gcagcggaag cgugcugggc cc                                 32
```

```
<210> SEQ ID NO 69
<211> LENGTH: 32
<212> TYPE: RNA
<213> ORGANISM: Homo sapiens

<400> SEQUENCE: 69
ggcagagugg cgcagcggaa gcgugcuggg cc                              32

<210> SEQ ID NO 70
<211> LENGTH: 28
<212> TYPE: RNA
<213> ORGANISM: Homo sapiens

<400> SEQUENCE: 70
gcagaguggc gcagcggaag cgugcugg                                   28

<210> SEQ ID NO 71
<211> LENGTH: 29
<212> TYPE: RNA
<213> ORGANISM: Homo sapiens

<400> SEQUENCE: 71
ugcagagugg cgcagcggaa gcgugcugg                                  29

<210> SEQ ID NO 72
<211> LENGTH: 29
<212> TYPE: RNA
<213> ORGANISM: Homo sapiens

<400> SEQUENCE: 72
gcaguggcgc agcggaagcg ugcugggcc                                  29

<210> SEQ ID NO 73
<211> LENGTH: 27
<212> TYPE: RNA
<213> ORGANISM: Homo sapiens

<400> SEQUENCE: 73
gcagaguggc gcagcggaag cgugcug                                    27

<210> SEQ ID NO 74
<211> LENGTH: 32
<212> TYPE: RNA
<213> ORGANISM: Homo sapiens

<400> SEQUENCE: 74
cgcagagucg cgcagcggaa gcgugcuggg cc                              32

<210> SEQ ID NO 75
<211> LENGTH: 31
<212> TYPE: RNA
<213> ORGANISM: Homo sapiens

<400> SEQUENCE: 75
cagagucgcg cagcggaagc gugcugggcc c                               31

<210> SEQ ID NO 76
<211> LENGTH: 31
<212> TYPE: RNA
<213> ORGANISM: Homo sapiens

<400> SEQUENCE: 76
agaguugcgc agcggaagcg ugcugggccc a                               31
```

-continued

```
<210> SEQ ID NO 77
<211> LENGTH: 27
<212> TYPE: RNA
<213> ORGANISM: Homo sapiens

<400> SEQUENCE: 77
gagauagcag aguggcgcag cggaagc                                            27

<210> SEQ ID NO 78
<211> LENGTH: 30
<212> TYPE: RNA
<213> ORGANISM: Homo sapiens

<400> SEQUENCE: 78
ggcucguugg ucuaggggua ugauucucgg                                         30

<210> SEQ ID NO 79
<211> LENGTH: 30
<212> TYPE: RNA
<213> ORGANISM: Homo sapiens

<400> SEQUENCE: 79
aggcucguug gucuaguggu augauucucg                                         30

<210> SEQ ID NO 80
<211> LENGTH: 30
<212> TYPE: RNA
<213> ORGANISM: Homo sapiens

<400> SEQUENCE: 80
gcccggauga uccucagugg ucuggggugc                                         30

<210> SEQ ID NO 81
<211> LENGTH: 26
<212> TYPE: RNA
<213> ORGANISM: Homo sapiens

<400> SEQUENCE: 81
uguagucgug gccgaguggu uaaggc                                             26

<210> SEQ ID NO 82
<211> LENGTH: 32
<212> TYPE: RNA
<213> ORGANISM: Homo sapiens

<400> SEQUENCE: 82
gacgaggugg ccgagugguu aaggcuaugg ac                                      32

<210> SEQ ID NO 83
<211> LENGTH: 32
<212> TYPE: RNA
<213> ORGANISM: Homo sapiens

<400> SEQUENCE: 83
gacgaggugg ccgagugguu aaggcuaugg au                                      32

<210> SEQ ID NO 84
<211> LENGTH: 31
<212> TYPE: RNA
<213> ORGANISM: Homo sapiens

<400> SEQUENCE: 84
gacgaggugg ccgagugguu aaggcuaugg a                                       31
```

```
<210> SEQ ID NO 85
<211> LENGTH: 31
<212> TYPE: RNA
<213> ORGANISM: Homo sapiens

<400> SEQUENCE: 85
gacgaggugg ccgagugguu aaggcaaugg a                              31

<210> SEQ ID NO 86
<211> LENGTH: 30
<212> TYPE: RNA
<213> ORGANISM: Homo sapiens

<400> SEQUENCE: 86
gacgaggugg ccgagugguu aaggcuaugg                                30

<210> SEQ ID NO 87
<211> LENGTH: 30
<212> TYPE: RNA
<213> ORGANISM: Homo sapiens

<400> SEQUENCE: 87
gacgaggugg ccgagugguu aaggcaaugg                                30

<210> SEQ ID NO 88
<211> LENGTH: 31
<212> TYPE: RNA
<213> ORGANISM: Homo sapiens

<400> SEQUENCE: 88
gccuggauag cucaguuggu agagcaucag a                              31

<210> SEQ ID NO 89
<211> LENGTH: 29
<212> TYPE: RNA
<213> ORGANISM: Homo sapiens

<400> SEQUENCE: 89
gccuggauag cucaguuggu agagcauca                                 29

<210> SEQ ID NO 90
<211> LENGTH: 32
<212> TYPE: RNA
<213> ORGANISM: Homo sapiens

<400> SEQUENCE: 90
ggcagagugg cgcagcggaa gcgugcuggg cc                             32

<210> SEQ ID NO 91
<211> LENGTH: 32
<212> TYPE: RNA
<213> ORGANISM: Homo sapiens

<400> SEQUENCE: 91
gcagaguggc gcagcggaag cgugcugggc cc                             32

<210> SEQ ID NO 92
<211> LENGTH: 28
<212> TYPE: RNA
<213> ORGANISM: Homo sapiens

<400> SEQUENCE: 92
gcagaguggc gcagcggaag cgugcugg                                  28
```

```
<210> SEQ ID NO 93
<211> LENGTH: 28
<212> TYPE: RNA
<213> ORGANISM: Homo sapiens

<400> SEQUENCE: 93
cggaagcgug cugggcccau aacccaga                                      28

<210> SEQ ID NO 94
<211> LENGTH: 29
<212> TYPE: RNA
<213> ORGANISM: Homo sapiens

<400> SEQUENCE: 94
ugcagagugg cgcagcggaa gcgugcugg                                     29

<210> SEQ ID NO 95
<211> LENGTH: 29
<212> TYPE: RNA
<213> ORGANISM: Homo sapiens

<400> SEQUENCE: 95
gcaguggcgc agcggaagcg ugcugggcc                                     29

<210> SEQ ID NO 96
<211> LENGTH: 27
<212> TYPE: RNA
<213> ORGANISM: Homo sapiens

<400> SEQUENCE: 96
gcagaguggc gcagcggaag cgugcug                                       27

<210> SEQ ID NO 97
<211> LENGTH: 32
<212> TYPE: RNA
<213> ORGANISM: Homo sapiens

<400> SEQUENCE: 97
cgcagagucg cgcagcggaa gcgugcuggg cc                                 32

<210> SEQ ID NO 98
<211> LENGTH: 31
<212> TYPE: RNA
<213> ORGANISM: Homo sapiens

<400> SEQUENCE: 98
cagagucgcg cagcggaagc gugcugggcc c                                  31

<210> SEQ ID NO 99
<211> LENGTH: 31
<212> TYPE: RNA
<213> ORGANISM: Homo sapiens

<400> SEQUENCE: 99
agaguugcgc agcggaagcg ugcugggccc a                                  31

<210> SEQ ID NO 100
<211> LENGTH: 31
<212> TYPE: RNA
<213> ORGANISM: Homo sapiens

<400> SEQUENCE: 100
gccuggauag cucaguuggu agagcaucag a                                  31
```

```
<210> SEQ ID NO 101
<211> LENGTH: 29
<212> TYPE: RNA
<213> ORGANISM: Homo sapiens

<400> SEQUENCE: 101
gccuggauag cucaguuggu agagcauca                                           29

<210> SEQ ID NO 102
<211> LENGTH: 32
<212> TYPE: RNA
<213> ORGANISM: Homo sapiens

<400> SEQUENCE: 102
uuccguagug uagugguuau cacguucgcc uc                                       32

<210> SEQ ID NO 103
<211> LENGTH: 30
<212> TYPE: RNA
<213> ORGANISM: Homo sapiens

<400> SEQUENCE: 103
uuccguagug uagugguuau cacguucgcc                                          30

<210> SEQ ID NO 104
<211> LENGTH: 32
<212> TYPE: RNA
<213> ORGANISM: Homo sapiens

<400> SEQUENCE: 104
uccguagugu agugguuauc acguucgccu ga                                       32

<210> SEQ ID NO 105
<211> LENGTH: 31
<212> TYPE: RNA
<213> ORGANISM: Homo sapiens

<400> SEQUENCE: 105
uccguagugu agugguuauc acguucgccu g                                        31

<210> SEQ ID NO 106
<211> LENGTH: 32
<212> TYPE: RNA
<213> ORGANISM: Homo sapiens

<400> SEQUENCE: 106
uccguagugu agugguuauc acguucgccu ca                                       32

<210> SEQ ID NO 107
<211> LENGTH: 30
<212> TYPE: RNA
<213> ORGANISM: Homo sapiens

<400> SEQUENCE: 107
uccguagugu agugguuauc acguucgccu                                          30

<210> SEQ ID NO 108
<211> LENGTH: 32
<212> TYPE: RNA
<213> ORGANISM: Homo sapiens

<400> SEQUENCE: 108
guuuccguag uguagugguc aucacguucg cc                                       32
```

-continued

<210> SEQ ID NO 109
<211> LENGTH: 28
<212> TYPE: RNA
<213> ORGANISM: Homo sapiens

<400> SEQUENCE: 109
ccguagugua gugguuauca cguucgcc                                              28

<210> SEQ ID NO 110
<211> LENGTH: 31
<212> TYPE: RNA
<213> ORGANISM: Homo sapiens

<400> SEQUENCE: 110
guuuccguag uguaguggguc aucacguucg c                                         31

<210> SEQ ID NO 111
<211> LENGTH: 27
<212> TYPE: RNA
<213> ORGANISM: Homo sapiens

<400> SEQUENCE: 111
cguaguguag ugguuaucac guucgcc                                               27

<210> SEQ ID NO 112
<211> LENGTH: 30
<212> TYPE: RNA
<213> ORGANISM: Homo sapiens

<400> SEQUENCE: 112
uccguagugu agugguuauc acuuucgccu                                            30

<210> SEQ ID NO 113
<211> LENGTH: 31
<212> TYPE: RNA
<213> ORGANISM: Homo sapiens

<400> SEQUENCE: 113
uccguagugu acugguuauc acguucgccu g                                          31

<210> SEQ ID NO 114
<211> LENGTH: 28
<212> TYPE: RNA
<213> ORGANISM: Homo sapiens

<400> SEQUENCE: 114
cguaguguag uggucaucac guucgccu                                              28

<210> SEQ ID NO 115
<211> LENGTH: 32
<212> TYPE: RNA
<213> ORGANISM: Homo sapiens

<400> SEQUENCE: 115 gggggguguag cucaguggua gagcgcgugc uu                                        32

<210> SEQ ID NO 116
<211> LENGTH: 31
<212> TYPE: RNA
<213> ORGANISM: Homo sapiens

<400> SEQUENCE: 116 gggggguguag cucaguggua gagcgcgugc u                                         31

```
<210> SEQ ID NO 117
<211> LENGTH: 30
<212> TYPE: RNA
<213> ORGANISM: Homo sapiens

<400> SEQUENCE: 117 gggggguguag cucaguggua gagcgcgugc                                    30

<210> SEQ ID NO 118
<211> LENGTH: 29
<212> TYPE: RNA
<213> ORGANISM: Homo sapiens

<400> SEQUENCE: 118 gggggguguag cucaguggua gagcgcgug                                     29

<210> SEQ ID NO 119
<211> LENGTH: 32
<212> TYPE: RNA
<213> ORGANISM: Homo sapiens

<400> SEQUENCE: 119
ggggggugua gcucaguggu agagcgcgug cu                                  32

<210> SEQ ID NO 120
<211> LENGTH: 32
<212> TYPE: RNA
<213> ORGANISM: Homo sapiens

<400> SEQUENCE: 120
uuggugguuc agugguagaa uucucgccug cc                                  32

<210> SEQ ID NO 121
<211> LENGTH: 31
<212> TYPE: RNA
<213> ORGANISM: Homo sapiens

<400> SEQUENCE: 121
uuggugguuc agugguagaa uucucgccug c                                   31

<210> SEQ ID NO 122
<211> LENGTH: 30
<212> TYPE: RNA
<213> ORGANISM: Homo sapiens

<400> SEQUENCE: 122
uuggugguuc agugguagaa uucucgccug                                     30

<210> SEQ ID NO 123
<211> LENGTH: 29
<212> TYPE: RNA
<213> ORGANISM: Homo sapiens

<400> SEQUENCE: 123
uuggugguuc agugguagaa uucucgccu                                      29

<210> SEQ ID NO 124
<211> LENGTH: 29
<212> TYPE: RNA
<213> ORGANISM: Homo sapiens

<400> SEQUENCE: 124
uggugguuca gugguagaau ucucgccug                                      29
```

```
<210> SEQ ID NO 125
<211> LENGTH: 31
<212> TYPE: RNA
<213> ORGANISM: Homo sapiens

<400> SEQUENCE: 125
auuggugguu cagugguaga auucucgccu g                          31

<210> SEQ ID NO 126
<211> LENGTH: 29
<212> TYPE: RNA
<213> ORGANISM: Homo sapiens

<400> SEQUENCE: 126
auuggugguu cagugguaga auucucgcc                             29

<210> SEQ ID NO 127
<211> LENGTH: 31
<212> TYPE: RNA
<213> ORGANISM: Homo sapiens

<400> SEQUENCE: 127
ggcauuggug guucaguggu agaauucucg c                          31

<210> SEQ ID NO 128
<211> LENGTH: 27
<212> TYPE: RNA
<213> ORGANISM: Homo sapiens

<400> SEQUENCE: 128
uuggugguuc agugguagaa uucucgc                               27

<210> SEQ ID NO 129
<211> LENGTH: 27
<212> TYPE: RNA
<213> ORGANISM: Homo sapiens

<400> SEQUENCE: 129
ugguucagug guagaauucu cgccucc                               27

<210> SEQ ID NO 130
<211> LENGTH: 29
<212> TYPE: RNA
<213> ORGANISM: Homo sapiens

<400> SEQUENCE: 130
cauugguggu ucagugguag aauucucgc                             29

<210> SEQ ID NO 131
<211> LENGTH: 31
<212> TYPE: RNA
<213> ORGANISM: Homo sapiens

<400> SEQUENCE: 131
agcauuggug guucaguggu agaauucucg c                          31

<210> SEQ ID NO 132
<211> LENGTH: 30
<212> TYPE: RNA
<213> ORGANISM: Homo sapiens

<400> SEQUENCE: 132
gcauuggugg uucaguggua gaauucucac                            30
```